(12) United States Patent
Taylor

(10) Patent No.: US 7,910,216 B2
(45) Date of Patent: Mar. 22, 2011

(54) PROCESS FOR THE PRODUCTION OF ORGANOSILSESQUIOXANES

(75) Inventor: Alan Taylor, Cambridge (GB)

(73) Assignee: The Welding Institute, Great Albington (GB)

( * ) Notice: Subject to any disclaimer, the term of this patent is extended or adjusted under 35 U.S.C. 154(b) by 823 days.

(21) Appl. No.: 11/424,513

(22) Filed: Jun. 15, 2006

(65) Prior Publication Data

US 2007/0122636 A1 May 31, 2007

(30) Foreign Application Priority Data

Nov. 28, 2005 (GB) .................................. 0524189.8

(51) Int. Cl.
*B32B 27/00* (2006.01)
*C08L 83/04* (2006.01)

(52) U.S. Cl. ............................ 428/447; 428/412; 528/12

(58) Field of Classification Search ................... 528/100, 528/10, 25, 28, 29, 34, 39, 33, 12; 428/412, 428/423.1, 447, 446, 28, 29, 34; 524/730, 524/806, 811, 833, 832, 836
See application file for complete search history.

(56) References Cited

U.S. PATENT DOCUMENTS

| 6,329,461 | B1 * | 12/2001 | Akiyama et al. ............... 524/730 |
| 6,586,104 | B2 | 7/2003 | Matsuda |
| 2003/0069350 | A1 * | 4/2003 | Yoshihara et al. ............ 524/588 |
| 2003/0191269 | A1 | 10/2003 | Ko et al. |
| 2003/0212228 | A1 | 11/2003 | Dai et al. |
| 2003/0224286 | A1 | 12/2003 | Barclay |
| 2005/0118429 | A1 * | 6/2005 | Taylor ........................... 428/412 |

FOREIGN PATENT DOCUMENTS

| BE | 538 417 | A | 7/1959 |
| EP | 0 410 564 | A2 | 1/1991 |
| FR | 1 469 074 | | 4/1967 |
| GB | 1 217 082 | A | 12/1970 |
| JP | 2004 284221 | A | 10/2004 |
| JP | 2005 122815 | | 5/2005 |
| WO | WO 01/10871 | | 2/2001 |

OTHER PUBLICATIONS

Cordes, et al., "Recent Developments in the Chemistry of Cubic Polyhedral Oligosilsesquioxanes", *Chem. Rev.* 2010, vol. 110, pp. 2081-2173, Department of Chemistry, Imperial College London, South Kensington, London SW7 2AZ, U.K., Published on Web Mar. 15, 2010.

* cited by examiner

*Primary Examiner* — James Seidleck
*Assistant Examiner* — S. Camilla Pourbohloul
(74) *Attorney, Agent, or Firm* — Workman Nydegger

(57) ABSTRACT

A process for forming a composition comprising organosilsesquioxanes, comprises the following steps:

1. partially hydrolysing hydrolysable inorganic monomer precursors comprising at least 50 mole % of first hydrolysable inorganic monomer precursors having the formula $RSiY_3$, in which R is an organic group, the R—Si bond is a non-hydrolysable bond, each Y group is the same as or different to one another and is selected from chemically-reactive groups such that each Si—Y bond is hydrolysable to form a Si—OH bond, to form inorganic monomers and allowing partial condensation of the inorganic monomers to form a liquid composition comprising inorganic oligomers;
2. prior to complete condensation of the inorganic monomers, quenching the liquid composition with an amount of water which, in combination with the water used in step (1) and any water liberated by condensation of the inorganic monomers in step (1), is in excess of the stoichiometric amount of water required to achieve complete hydrolysis of all the hydrolysable inorganic monomer precursors present; and
3. drying the composition.

37 Claims, No Drawings

PROCESS FOR THE PRODUCTION OF ORGANOSILSESQUIOXANES

FIELD OF THE INVENTION

The present invention relates to a process for the production of organosilsesquioxanes, and to the use of a composition comprising organosilsesquioxanes to provide a protective coating on a substrate so as to impart to the substrate resistance to mechanical and chemical damage, while at the same time maintaining excellent optical properties, and as a bulk material.

BACKGROUND TO THE INVENTION

Organosilsesquioxanes are silicon-oxygen based frameworks having the general formula $(RSiO_{1.5})_n$, in which n is an even number $\geq 4$. Organosilsesquioxanes which have a very specific structure, for example a compound having the formula $(RSiO_{1.5})_8$ has an octahedral cage structure, are referred to in the field as organooligosilsequioxanes or polyhedral oligomeric silsesquiloxanes (or POSS®).

Organosilsesquioxanes have the potential to offer good mechanical properties, for example as coatings with good abrasion resistance, and can be formulated to have good chemical resistance, for instance as embodied by hydrolytic stability or stability to UV degradation. These and other properties render the organosilsesquioxanes useful as protective coatings for a wide variety of substrates, particularly polymer-based materials, such as acrylic polymers and polycarbonates, which are routinely used as alternatives to glass in many situations where the weight, tendency to shatter or expense of glass contraindicates its use.

A number of processes for the manufacture and modification of organosilsesquioxanes is described in the literature, including:

(1) the manufacture of partially or fully condensed structures;

(2) the functionalisation of partially or fully condensed structures; and (3) the manufacture of structures containing more than one organic functionality.

Examples of such processes are disclosed by Brown et al, J. Am. Chem. Soc. (1965) 87:4313-4317 and Feher en al, J. Am. Chem. Soc. (1989)111:1741-1748. In general terms, these processes the use of very low monomer concentrations in solvent and the addition thereto of large amounts of water, to allow the very slow production, typically over a number of months, of specific and defined cage structures. As a result, the materials produced have limited application, for instance in the field of protective coatings, due to the considerable expense associated with their slow production.

The incorporation of functional organic ligands into the basic organosilsesquioxanes structure has been achieved through a number of routes. In this context, the term "functional" is used to describe organic groups that act to impart particular mechanical and/or chemical properties to the final material. For example, the incorporation of organic ligands has been achieved by:

(1) exchange of functionality in an existing fully condensed structure;

(2) cleavage and insertion of functionality into a fully condensed structure;

(3) addition of functionality into a partially condensed structure; and (4) incorporation of functionality during the fabrication of the structure.

Examples of these processes are described in U.S. Pat. No. 5,047,492 and U.S. Pat. No. 5,484,867.

The last of the above routes, (4), is rarely performed, but where it is it involves co-hydrolysis and condensation of silane precursors containing non-functional organic groups and silane precursors containing functional organic groups particularly with the ability to polymerise. However, the preparation of these functionalised organosilsesquioxanes remains slow.

It would, therefore, be desirable to provide a process for the preparation of organosilsesquioxanes, and compositions comprising the same, which is not subject to the lengthy reaction times described in the prior art, and which therefore makes these materials available to the industry on a more cost-effective basis.

SUMMARY OF THE INVENTION

According to a first aspect of the present invention, a process for preparing a composition comprising organosilsesquioxanes comprising the following steps:

(1) partially hydrolysing hydrolysable inorganic monomer precursors comprising at least 50 moles % of first hydrolysable inorganic monomer precursors having the formula $RSiY_3$, in which R is an organic group, the R—Si bond is a non-hydrolysable bond, each Y group is the same as or different to each other Y group and is selected from chemically-reactive groups such that each Si—Y bond is hydrolysable to form a Si—OH bond, to form inorganic monomers, and allowing partial condensation of the inorganic monomers to form a liquid composition comprising inorganic oligomers;

(2) prior to complete condensation of the inorganic monomers, quenching the liquid composition with an amount of water which, in combination with the water used in step (1) and any water liberated by condensation of the inorganic monomers in step (1), is in excess of the stoichiometric amount of water required to achieve complete hydrolysis of all the hydrolysable inorganic monomer precursors present; and (3) drying the composition.

The process of the present invention allows for the controlled and rapid manufacture of a wide variety of organosilsesquioxanes-based compositions. The compositions may comprise organosilsesquioxanes having one or more organic functionalities and/or having completely or incompletely condensed structures. Furthermore, the compositions may or may not comprise only organo-oligosesquioxanes.

According to a second aspect of the present invention, composition comprising organosilsesquioxanes are obtainable by the above-described process.

Other aspects of the present invention include the application of the above-described compositions to a variety of substrates, the coated substrates themselves, articles made from the above-described compositions, and use of the above-described compositions as bonding agents.

The compositions of the present invention are capable of providing coatings that confer abrasion resistance, hydrolytic stability and stability to UV degradation to a wide variety of substrates, particularly plastics substrates, and can be fine tuned to have other properties depending upon the nature of the functionalities incorporated therein and the conditions utilised in their preparation.

DETAILED DESCRIPTION OF THE INVENTION

In general terms, the process of the present invention involves a two-step hydrolysis/condensation reaction and subsequent drying, and optionally curing, of the resulting composition. In the first step, hydrolysable inorganic monomer precursors, of which at least 50 mole % have the formula RSiY₃ (referred to as "first" hydrolysable monomer precursors"), are partially hydrolysed and allowed to undergo some condensation, but not complete condensation, to form inorganic oligomers that will form the building blocks for the final organosilsesquioxanes molecules.

In the second step of the process, the inorganic oligomers are quenched by addition to, or addition thereto, of a relatively large amount of water, which has the effect of causing rapid condensation of the inorganic oligomers. Depending on the time allowed and the conditions used for condensation the degree of condensation may vary somewhat, up to essentially complete condensation of those oligomers.

The precise nature of the final structures formed on drying, and optionally curing, the composition produced is a matter for conjecture, but is not important given the beneficial mechanical and chemical properties achieved.

In the context of the present Application, by an "hydrolysable inorganic monomer precursor", we mean any inorganic molecule which is activated by hydrolysis to a polymerisable inorganic monomer, which, on polycondensation with similar hydrolysed or partially hydrolysed monomers, forms inorganic oligomers, and ultimately an inorganic network. The term "inorganic" is used to denote the presence in the precursor molecule of an inorganic element, typically one giving rise to an oxide ceramic material, e.g. silicon, aluminium, titanium, zirconium, yttrium, or other transition metals.

Considering the first step of the process in more derail, the first hydrolysable inorganic monomer precursors, RSiY₃, may be selected from a variety of materials. However, it is critical that the R—Si bond should not be hydrolysable, as otherwise the organic group R may be lost to the final structure. It is preferred that group R itself is chemically stable, and in particular that it is stable to hydrolysis in the presence of water or moisture. Suitable examples of the group R include hydrogen, and optionally substituted (cyclo)alkyl, aryl, alkenyl, amido, epoxy, (meth)acrylic, styrenic, nitrile, anhydride, ester, phosphino, halide, amino, mercapto and cyanate groups, and mixtures thereof. Preferred R groups are selected from (cyclo)alkyl, aryl and alkenyl groups, optionally substituted with groups selected tram epoxy, vinyl, (meth)acrylic and cyanate groups.

It is further preferred that the size of the R group be selected so that the final composition is liquid in nature, enabling its application as a coating composition.

The Y groups in the first hydrolysable inorganic monomer precursors may be the same as or different to one another, although typically they are the same. The Si—Y bond is a highly reactive bond which readily undergoes hydrolysis to form a silanol group, ie. Si—OH. Suitable examples of Y groups are alkoxy, acetoxy groups, amine and nitrate groups and halogen atoms. Once formed, a silanol group can condense via a water-liberating reaction with another silanol group according no the following reaction sequence:

$$RY_{3-n}Si(OH)_n + (HO)_n SiY_{3-n}R \rightarrow RY_{3-n}Si-O-Si(OH)_{n-1}Y_{3-n}R$$

Alternatively, condensation may proceed in a heterofunctional manner when different hydrolysable inorganic monomer precursors are present, as is discussed in more detail below, such as shown in the following two reaction sequences:

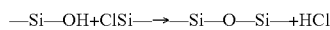

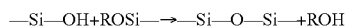

The process of the present invention may involve the use of a single type of hydrolysable inorganic monomer precursor, having the formula RSiY₃. Alternatively, different hydrolysable inorganic monomer precursors may be used, for instance differing in the nature and/or number of organic groups R and/or the nature and/or number of the hydrolysable groups Y.

By way of example, first hydrolysable inorganic monomer precursors may be used having different R groups, for instance RSiY₃, R¹SiY₃, etc., the R and R¹ groups being selected to provide particular mechanical and/or chemical properties in the final product. In this regard, the present invention is not limited to the use of two different types of first hydrolysable monomer precursors, but may involve the use of more than two different types of the monomer precursors, provided that adequate control over the process is maintained so as to achieve the desired level of incorporation of the different R groups into the final product.

As mentioned above, and in addition or alternatively to the use of first hydrolysable inorganic monomer precursors having different R and/or Y groups, the process may involve the use of hydrolysable inorganic monomer precursors differing in the number of hydrolysable groups Y. In particular, hydrolysable inorganic monomer precursors having the general formula $R_n SiY_{4-n}$, in which n is 0, 2 or 3, R is an organic group, for instance selected from those groups given for R above, the R—Si bond is a non-hydrolysable bond, and the R groups are the same as or different to one another, and each Y group is the same as or different to each other Y group and is selected from chemically-reactive groups such that each Si—Y bond is hydrolysable to form a Si—OH bond, and mixtures of such monomer precursors, may be used in addition to the first hydrolysable monomer precursors, RSiY₃. In the following, these additional monomer precursors are termed "second hydrolysable inorganic monomer precursors".

By way of example, hydrolysable inorganic monomer precursors having four hydrolysable bonds, ie., having the formula SiY₄ (n=0), may be used in addition to the first hydrolysable inorganic monomer precursors.

In addition, or alternatively, the process may involve the use of hydrolysable inorganic monomer precursors having fewer hydrolysable bonds than the first hydrolysable inorganic monomer precursors, for instance having a formula selected from R₂SiY₂ (n=2) and R₃SiY (n=3), and mixtures thereof.

In the context or any of the second hydrolysable inorganic monomer precursors mentioned above, the nature of the groups R and Y are as defined above for the first organic monomer precursors. For clarity, however, the groups R and/or Y in the second hydrolysable inorganic monomer precursors may be the same as or different to the groups R and/or Y in the first hydrolysable inorganic monomer precursors.

Suitable examples of first hydrolysable inorganic monomer precursors and second hydrolysable inorganic monomer precursors having the formula RSiY₂ or R₃SiY include:

(i) (alkyl)alkoxysilanes such as trimethoxysilane, tri-ethoxysilane, tri-n-propoxysilane, dimethoxysilane, di-ethoxysilane, di-iso-propoxysilane, monomethoxysilane, monoethoxysilane, monobutoxysilane, methyldimethoxysilane, ethydiethoxysilane, dimethylmethoxysilane, di-iso-propyl-isopropoxysilane, methyltrimethoxysilane, ethyltriethoxy-silane, n-propyltri-n-propoxysilane, butyltributoxysilane, dimethyldimethoxysilane, diethyldiethoxysilane, di-iso-propyl-di-iso-propoxysilane, dibutyldibutoxysilane, tri-methylmethoxysilane, triethylethoxysilane, tri-n-propyl-n-propoxysilane, tributylbutoxysilane, phenyltrimethoxy-silane, diphenyldiethoxysilane and triphenylmethoxysilane;
(ii) (alkyl)alkoxysilanes having an isocyanato group such as 3-isocyanatopropyltrimethoxysilane, 3-isocyanatopropyltriethoxysilane, 3-isocyanatopropylmethyldimethoxysilane, 3-isocyanatopropylethyldiethoxysilane, 3-isocyanatopropyl-dimethyl-isopropoxysilane, 3-isocyanatopropyldiethyl-ethoxysilane, 2-isocyanatoethyldiethylbutoxysilane, di(3-isocyanatopropyl)diethoxysilane, di(3-isocyanatopropyl)-methylethoxysilane, and ethoxytriisccyanatosilane;
(iii) (alkyl)alkoxysilanes having an epoxy group such as 3-glycidoxypropyltrimethoxysilane, 3-glycidoxypropyltri-ethoxysilane, 3-glycidoxypropylmethyldimethoxysilane, 3-glycidoxypropylmethydiethoxysilane, 3-glycidoxypropyldi-methyl ethoxysilane, 2-(3,4-epoxycyclohexyl)ethyltrimethoxy-silane, and 3,4-epoxybutyltrimethoxysilane;
(iv) (alkyl)alkoxysilanes having a carboxyl group such as carboxymethyltriethoxysilane and carboxymethylethyldiethoxysilane;
(v) alkoxysilanes having an acid anhydride group such as 3-(triethoxysilyl)-2-methpropylsuccinic anhydride;
(vi) alkoxysilanes having an acid halide group such as 2-(4-chlorosulphonylphenyl)ethyltriethoxysilane;
(vii) (alkyl)alkoxysilanes having an amino group such as N-2-(aminoethyl)-3-aminopropyltriethoxysilane, N-2-(aminoethyl)-3-aminopropylmethyldimethoxysilane, and N-phenyl-3-aminopropyltrimethoxysilane;
(viii) (alkyl)alkoxysilanes having a thiol group such as 3-mercapcopropyl-trimethoxy-silane, 3-mercaptopropyltriethoxysilane, 2-mercaptoethyltriethoxysilane, and 3-mercaptopropylmethyldimenthoxysilane;
(ix) (alkyl)alkoxysilanes having a vinyl group such as vinyltrimethoxysilane, vinyltriethoxysilane, and vinyl-methyldiethoxysilane;
(x) (alkyl)alkoxysilanes having an acrylate or methacrylate group such as 3-methacryloxy-propyltrimethoxysilane, 3-methacryloxyproply-triethoxysilane, 3-methacryloxypropylmethyldimethyl-silane and 3-acryloxypropyltriethoxysilane;
(xi) (alkyl)alkoxysilanes having a halogen atom such as triethoxyfluorosilane, 3-chloropropyltrimethoxysilane, 3-bromoalkylalkoxysilane, and 2-chloroethylmethyldimethoxy-silane;
(xii) (alkyl)alkoxysilanes having an halogenated alkyl ligand such as (3,3,3-trifluoropropyl)trimethoxysilane and 1H,1H,2H,2H-perfluorodecyltriethoxysilane; and
(xiii) (alkyl)alkoxysilanes employing an alkoxy group as a functional group such as isopropyltri-isopropoxysilane and tri-isopropylisopropoxysilane.

In the above compounds the alkyl group may be replaced by cycloalkyl group, an aryl group or an alkenyl group, and may optionally be substituted preferably with a (meth)acrylate group or an epoxy group. Where hydrolytic stability is desired in the final product, those hydrolysable monomer precursors having hydrolysable R groups should be avoided.

Suitable examples of second hydrolysable inorganic monomer precursors having the formula SiY, include silicon tetra-alkoxides, such as tetramethoxysilane, tetramethoxysilane, tetraisopropoxy-silane and tetrabutoxysilane.

The process may also, or alternatively, involve the use of hydrolysable inorganic monomer precursors containing an inorganic atom other than silicon, for instance having the formula $MY_n$, in which M is typically a metal, n is the valency of the metal, and each Y group is the same or different to one another and is selected from chemically-reactive groups such that each M-Y bond is hydrolysable to a M-OH bond.

Suitable examples of such materials include:
i) titanium tetra-alkoxides such as titanium tetra-n-propoxide, titanium tetra-iso-propoxide and titanium tetrabutoxide;
ii) aluminium tetra-alkoxides such as aluminium tri-secbutoxide, aluminium tri-n-butoxide aluminium tri-isopropoxide;
iii) zirconium tetra-alkoxides such as zirconium tetra-n-propoxide, zirconium tetra-iso-propoxide and zirconium tetrabutoxide; and
iv) metal alkoxides such as copper dimethoxide, barium diethoxide, boron trimethoxide, gallium triethoxide, germanium tetraethoxide, lead tetrabutoxide, tantalum penta-n-propoxide and tungsten hexaethoxide.

The process may also, or alternatively, involve the use of hydrolysable inorganic monomer precursors of the generic formula $(R_2Si)_xY_2$, in which $x \geq 1$, the R—Si bond is a non-hydrolysable bond and R is defined above (and each R group may be the as as or different to each other R group) and Y is a chemically reactive group with each Si—Y bond being hydrolysable to Si—OH. Suitable examples of the group Y (which may be the same as or different to one another) include chlorine, acetoxy, amine, oxime (ie., $R_2C$=NOSi) and alkoxy, The integer x may vary from 1 to a large number, for instance up to or even greater than 100, giving rise no multi-silicon polymers.

When the process involves the use of hydrolysable inorganic monomer precursors which differ in the number of hydrolysable groups present, it is critical that at least 50 mole %, preferably more than 60 mole %, more preferably at least 70 mole % and most preferably at least 80 mole % or higher, for instance at least 90 mole %, of the total hydrolysable inorganic monomer precursors present should be first hydrolysable inorganic monomer precursors, in order to obtain the most desirable properties for coating applications.

The hydrophilic/hydrophobic character of the R groups(s) will determine the behaviour of the final product when exposed to water. This behaviour can be modified by appropriate selection of solvent. For example, the tendency towards the repulsion of water of an aliphatic hydrocarbon can be changed by the use of a protic solvent, such as alcohol, compared to an aprotic one, such as tetrahydrofuran.

When the process involves the use of different hydrolysable inorganic monomer precursors it is preferred that hydrolysis of the different hydrolysable inorganic monomer precursors be conducted separately so as to avoid competition for the water molecules present, which may otherwise result in an inhomogeneous or undesirable distribution or monomers, and in particular the organic groups associated therewith, in the final product. After separate partial hydrolysis, the different inorganic oligomers formed are mixed together prior to subjecting to the quenching step that is to follow.

In order to hydrolyse the hydrolysable inorganic monomer precursors, water is either added to the hydrolysable inorganic monomer precursors, or is synthesised in situ. Typically, hydrolysis is achieved by formation of an homogeneous mixture with water and, optionally, an organic solvent. Alternatively, the precursors may be dissolved in an organic solvent and water added to the resulting solution in a controlled manner, to avoid the uncontrolled development of agglomerations of partially-hydrolysed molecules. Suitable organic solvents include low boiling point organic liquids, for instance having a boiling point lower than 100° C., such as alcohols.

Preferably, the mixture of water and hydrolysable monomer precursors is mixed to ensure that as many precursor molecules are exposed to water as possible, thereby achieving as homogeneous hydrolysis and condensation as possible.

If, as is less preferred, water is to be synthesized in situ in the reaction mixture, this can be achieved, for example, by adding an alcohol to the hydrolysable inorganic monomer precursors and then a weak acid, for example acetic acid, again in a controlled manner. In this case, and as described above, it is preferred that separate partial hydrolysis of different hydrolysable inorganic monomer precursors is carried out, followed by mixing together of the different inorganic oligomers formed.

A catalyst may be used to initiate hydrolysis of the hydrolysable inorganic monomer precursors, provided that the catalyst does not react with the inorganic monomer precursors, or affect the nature of the species formed on hydrolysis. Suitable catalysts include mineral acids such as hydrochloric acid, sulphuric acid and nitric acid. Only a small amount of acid is needed for this purpose. Although, depending upon the nature of the inorganic monomer precursors, hydrolysis may proceed spontaneously.

The amount of water used for hydrolysis should generally be sufficient to hydrolyse at least one of the hydrolysable bonds present in each of the inorganic monomer precursor molecules. However, preferably the amount of water, and the conditions of the hydrolysis reaction, are selected so as to achieve hydrolysis of only one or at most two of the hydrolysable bonds present in the first hydrolysable inorganic monomer precursors, as this will dictate the types or structure that are achieved in the second step of the process.

As explained above, part of the first step of the process involves at least partial condensation, but not complete condensation, of the monomers formed on hydrolysis to form inorganic oligomers. The degree of condensation which takes place may be determined by, for example, NMR. Preferably the degree of condensation is such that the majority of oligomers formed from first hydrolysable monomer precursors have one of the following formulae in which each or some of the R groups may be the same or different:

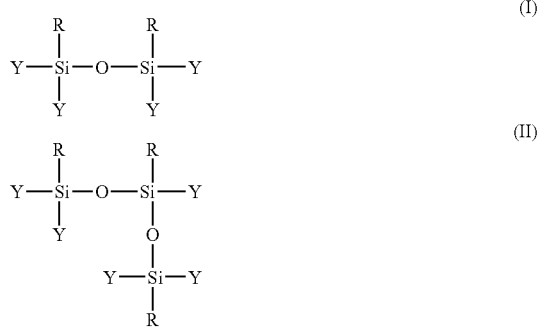

More preferably a majority of the oligomers have the formula (I), and most preferably most (for instance at least 80 mole % or even at least 90 mole %) of the oligomers have the formula (I).

The first, hydrolysis, step of the process can vary in duration, for instance it may take less than an hour or many days, depending upon the properties required in the final product. Longer durations are believed no result in greater connectivity of the resulting inorganic network, and thus greater molecular weight.

Once sufficient time for some condensation to occur, or for the desired degree of condensation to occur, has lapsed, the mixture is quenched into water to fully hydrolyse the species present and to create conditions that favour complete hydrolysis and further condensation. The detailed nature of the structures created depends upon the nature and concentration of the hydrolysable inorganic monomer precursors used, the solvent, the initial hydrolysing conditions and the co-condensation conditions (time, temperature, pH). In practice, the hydrolysis and condensation reactions of the first step of the process may be allowed to proceed for a period ranging from a matter of minutes, typically at least 10 minutes, to 24 hours or more.

Quenching can be achieved either by adding water to the liquid composition obtained in the first step of the process, or by adding the liquid composition to water, preferably in a single step. The volume of water used in the quenching step, in combination with any water used in the first step of the process and any water liberated as a result or condensation in than step, should be greater than the stoichiometric amount of water required to achieve total hydrolysis (ie. of all hydrolysable bonds) of all the hydrolysable inorganic monomer precursors. Preferably, the amount of water is at least twice, and more preferably at least five times, this stoichiometric amount. Further condensation is then allowed to proceed, with stirring, typically for a matter of hours up to a number of days, depending upon the properties required in the final product, and whether it is desired that this product should be only partially condensed or essentially completely condensed.

The resulting product is then dried. In the context of this Application "drying" includes the removal of any free water and volatiles, for instance by heating to elevated temperature, typically in the range 40 co 80° C.

The dried product is then ready for use, for instance as a coating composition, or in bulk form, or it may be further modified prior to use. For instance, the product may be cross-linked (or cured) and/or modified to include further organic character to thereby modify the properties of the final product, and/or it may be dehydrated, to reduce or prevent further reaction during use. Solvent may be added to the composition, to improve shelf-life.

Cross-linking, or curing, of the product may be achieved through the dependent organic R groups, and/or via residual silanols, to form a variety of 3-dimensional structures.

Cross-linking of the organic groups may be achieved by any of the conventional means, for instance by the use of suitable cross-linking reagents or processing conditions, or both, selected to promote intermolecular cross-linking rather than intramolecular cross-linking. For example, epoxy-containing R groups may be cross-linked, or further polymerised, using reagents which act as accelerators or hardeners, for instance amines, or using Lewis acids.

While the dried product might not contain many residual silanols, these can nonetheless influence the behaviour of the product during curing and after curing. Condensation of some or all of these residual silanols may be particularly desirable where further condensation during use of the product would adversely affect the properties of the product. The residual silanols can be made to undergo self-condensation by the use of suitable condensation catalysts, such as triethylamine or tin catalysts, such as tin (II) ethyl hexanoate, or by the selection of suitable reaction conditions known in the art.

Alternatively, condensation of residual silanols may be achieved by the addition of further silanol-containing species or other species condensable with the residual silanols already present in the product. Suitable materials are those having the generic formula $R_nSiY'_{4-n}$, in which n is 0 to 3, R is an organic group as defined above, with each R—Si bond being a non-hydrolysable bond and each R group being the same as or different to each other R group, and Y' is a species that will allow siloxane formation through silanol condensation or other routes, with each Y' group being the same as or different to each other Y' group.

For instance, silanol-containing species for use in said condensation may be prepared by hydrolysis of hydrolysable inorganic monomer precursors having the generic formula $R_nSiY'_{4-n}$, in which each Si—Y' bond is hydrolysable to Si—OH, with Y' being selected, for instance, from those groups given for Y above in the context of first hydrolysable inorganic monomer precursors. Such hydrolysis results in species such as, but not limited to, $R_2Si(OH)_2$ and $R_3Si(OH)$.

Typically, these silanol-containing species will be added to the dried product in the presence of a condensation agent, such as tin (II) ethyl hexanoate, to promote condensation.

Another option mentioned above to effect condensation of the residual silanols is to add other species condensable with those silanols and having the generic formula $R_nSiY'_{4-n}$, in which the Si—Y' bond might not be hydrolysable directly, or at all, to Si—OH. Such species include materials commonly used as derivatising agents to render glass surfaces hydrophobic, and examples of such materials are well known in the art. For instance, materials having the generic formula $R_3SiY'$ are suitable for this purpose, in which R is as defined above and Y' is, for instance, chlorine. For instance, one particular example or such a derivatising agent is trimethylchlorosilane.

Yet another option to effect silanol condensation is to use a material having the generic formula $(R_2Si)_xY_2$, as defined above in the context of the second hydrolysable inorganic monomer precursors, and to hydrolyse this prior to addition to the dried product.

In addition to, or as an alternative to, reducing the residual silanol content by condensation, this may be achieved via at least partial dehydration, and preferably substantially complete dehydration. Dehydration is achieved by any of the conventional methods known in the art. For instance, the dried product may be dissolved in any suitable solvent, for instance tetrahydrofuran (THF), and free water removed via a molecular sieve. Alternatively, dehydration can be further aided by the use of a condensation catalyst, such as triethylamine dissolved in THF and placed over a molecular sieve. After a period of dehydrating the dried product, the volatile solvent is evaporated off to leave a fully or partially dehydrated product.

While, in the above, further condensation of residual silanols has been described as conducted on the dried product, it might be desirable to effect some condensation prior to drying or prior to complete drying of the product. For instance, it might be desirable to effect condensation on a product that has been at least partially dehydrated after drying to remove free water.

Further, while dehydration has been described above as conducted on the dried product, at least partial dehydration may be conducted at earlier stages in the process.

The process of the present invention is capable of giving rise to a wide variety of product structures. The tendency towards a "cage" or "ladder" structure in the final product is controlled by the process parameters, for instance the type and/or concentration of the oligomers formed; the solvent employed; the time and temperature of the mixing step; the concentration during the quenching step; the time and temperature under which quenching is carried out; and the method of recovering the final product.

Should the cross-linked density of the product be less than the theoretical 100%, the product can still be considered to be reactive, which may or may not be acceptable according co the application to which the material is to be put. If this is unacceptable, various options to achieve further cross-linking, and to reduce reactivity, are described above.

For coating applications, cross-linking through organic (ie. R) groups may be initiated prior to coating, and taken to completion either prior to coating or after coating, on to a substrate, for instance using known irradiation (eg. UV), thermal or chemical methods. If cross-linking is taken to completion prior to coating it may be desirable to dissolve the composition in a solvent in order to coat the composition on to a substrate, and then to evaporate the solvent in order to dry the coated composition.

Before or after any cross-linking, or further condensation, the product obtained on drying (the third step of the process), may be mixed with an organic monomer or oligomer (generally referred to in the following as "polymerisable organic species"), which may then be further polymerised, or an organic polymer, such as a latex.

The nature of the polymerisable organic species is selected according to the properties required in the final product. Typically, the polymerisable organic species will be selected co provide strength and abrasion-resistance and, where desired, transparency. Furthermore, if chemical resistance is required, for instance resistance to swelling or other damage on contact with a solvent, it is desirable to employ polymerisable organic species capable of forming two-dimensional or three-dimensional, i.e. cross-linked, polymer networks. Such polymerisable organic species may be considered as having difunctional or trifunctional reactivity, in that they possess two or more reactive sites available for polymerization.

For coating applications, preferred polymerisable organic species are those which, upon polymerization, form thermosetting polymers. Examples of suitable polymerisable organic species include carbonates, esters such as terephthalates, epoxy-containing materials, methyl(meth)acrylates, urethanes, and other difunctional or trifunctional monomers such as some urethane acrylates, unsaturated aliphatic hydrocarbons, and mixtures thereof. Urethane precursors, such as isocyanates or diisocyanates and polyols, and urethane acrylates are particularly preferred, Organometallic monomers may also be used, but in this case they will not contain hydrolysable bonds.

Preferably, the polymerisable organic species polymerise at relatively low temperature, e.g. lower than 150° C., after addition of a suitable initiator, or by irradiation, e.g. with UV or IR light, or bombardment with X-rays or electron beams, so as to be applicable as coatings for thermoplastic materials or thermosetting materials having low melting points.

Polymerisation of the polymerisable organic species may be initiated in any conventional manner, which will be determined by the nature of the polymerisable organic species. It will normally involve the use of a polymerization initiator.

For coating applications, substantial organic polymerisation is usually delayed until after coating on to a substrate. Therefore, if heat is used to initiate or accelerate organic polymerisation, the temperature should be selected so as not to have any deleterious effect on the substrate to which the coating is to be applied. In the case of thermoplastic or thermosetting substrates, relatively low temperatures should be used, typically lower than 150° C., and more typically in the range 30 to 80° C. Where a chemical polymerization initiator is used, this may mean delaying addition of this until just prior to, or possibly during, the coating operation.

The proportion of organic polymer incorporated into the final product depends on the properties required in the final products.

The properties of the final product may be further adjusted through the use of additives conventional in the art.

When used as a coating composition, the composition may be applied to a substrate by any conventional means, for example dipping, spraying, roll coating or brushing. The composition may be applied to a wide variety of substrates, and is particularly suitable coating polymeric materials having relatively low melting points, for example of 150° C. or lower. Examples of such polymeric materials include thermoplastic materials and thermosetting materials such as polycarbonates, polyesters such as polyacrylates and polyterephthalates, polyurethanes, and polyacrylics. The enhanced scratch/abrasion and chemical resistance imparted no these materials by way of the coatings of the present invention allows them to be considerably more widely utilised than they are at present.

The coating composition may also be used to coat substrates selected from glass, metals including soft metals such as aluminium, brass and silver, ceramic materials, and natural materials such as leather and wood, or synthetic substitutes for these materials. It finds particular use as a coating for glass, and glass substitutes. For example, it may be used to coat building or vehicle, windows and windscreens, e.g. for automobile, aircraft and trains; spectacle lenses; camera lenses; protective visors; optical filters and light casings, e.g. headlamp clusters; compact discs; display screens, e.g. in personal computers and mobile phones; and to protect white goods, e.g. refrigerators and washing machines, and brown goods e.g. audiovisual equipment.

The composition of the present invention also finds use as a catalyst coating on a variety of substrates. For this application it is preferred that the composition should not be cross-linked, so as to maintain its liquid nature.

The composition of the present invention also finds use in bonding together at least two articles. For instance, the composition may be applied to the surface of one or each article, the surfaces to be bonded brought together, and the composition cured to form a secure bond.

The process of the present invention is also capable of producing materials which rind use as bulk materials rather than as coatings. In this case, the material may be shaped, for instance by moulding, or otherwise formed into a wide variety of different articles.

The present invention is further illustrated by the following Examples.

EXAMPLES

Example 1

Methacrylate Silane Resin

A mixture of 111.1 g of industrial methylated spirit (IMS), 16.3 g of water and 0.16 g of 37% HCl were thoroughly stirred and then added to 150.0 g 3-trimethoxysilylpropyl methacrylate. This mixture was stirred vigorously for 4 hours, and was then poured (or quenched) into 555 g of distilled water. The quenched mixture was stirred vigorously for at least 18 hours before being poured into a large polypropylene container and heated at approximately 50° C. for approximately 6 hours to remove the water. The remaining viscous liquid (resin) was then recovered.

Example 2

Methacrylate Silane Coating 10.0 g of the resin produced in Example 1 was diluted with 30.0 g of IMS and 0.1 g of the photoinitiator Irgacure 184 was added. After thorough mixing this solution was flow coated onto a Lexan polycarbonate plaque. The coated plaque was dried in an air atmosphere for 5 minutes at 50° C. and then cured using UV light.

Example 3

Methacrylate Silane and Urethane Acrylate Coating 9.0 g of the resin produced in Example 1 was diluted with 27.0 g of industrial methylated spirit and stirred to give an homogeneous solution. To this solution 1.0 g of aliphatic urethane acrylate 260GP25 was added and 0.1 g of the photoinitiator Irgacure 184. After stirring to achieve an homogeneous solution, the liquid was deposited by flow coating onto a Lexan polycarbonate plaque. The coated plaque was dried in an air atmosphere for 5 minutes at 50° C. and then cured using UV light.

Example 4

Acrylate Silane Resin

A mixture of 117.8 g of industrial methylated spirit (IMS), 17.3 g of water and 0.17 g of 37% HCl were thoroughly stirred and then added to 150.0 g 3-trimethoxysilylpropyl acrylate. This mixture was stirred vigorously for 4 hours, and was then poured (or quenched) into 570 g of distilled water. The quenched mixture was stirred vigorously for at least 18 hours before being poured into a large polypropylene container and heated at approximately 50° C. for 6 hours to remove the water. The remaining viscous liquid (resin) was then recovered.

Example 5

Acrylate Silane Coating 10.0 g of the resin produced in Example 4 was diluted with 30.0 g of IMS and 0.1 g of the photoinitiator Irgacure 184 was added, as was 0.1 g of FC4430 (from 3M Corporation) as a flow agent. After thorough mixing this solution was flow coated onto a Lexan polycarbonate plaque. The coated plaque was dried in an air atmosphere for 5 minutes at 50° C. and then cured using UV light.

Example 6

Acrylate Silane and Urethane Acrylate Coating 9.0 g of the resin produced in Example 4 was diluted with 27.0 g of industrial methylated spirit and stirred to give an homogeneous solution. To this solution 1.0 g of aliphatic urethane acrylate 260GP25 was added and 0.1 g of the photoinitiator Irgacure 184. After stirring to achieve an homogeneous solution, the liquid was deposited by flow coating onto a Lexan polycarbonate plaque. The coated plaque was dried in an air atmosphere for 5 minutes at 50° C. and then cured using UV light.

Example 7

Epoxy Silane Resin

A mixture of 77.9 g of industrial methylated spirit (IMS) and 11.4 g of distilled water were thoroughly stirred and then added to 100.0 g of 3-glycidoxypropyltrimethoxy-silane. This mixture was stirred vigorously for 4 hours, and was then poured (or quenched) into 379 g of distilled water. The quenched mixture was stirred vigorously for at least 18 hours before being poured into a large polypropylene container and heated at approximately 50° C. for approximately 6 hours to remove the water. The remaining viscous liquid (resin) was then recovered.

Example 8

Epoxy Silane and Diaminooctane Coating 5.0 g of the resin produced in Example 7 was diluted in 15.0 g of IMS and stirred to give an homogeneous liquid. To this liquid was added 1.08 g of diaminooctane. The mixture was vigorously stirred for 5 minutes and then deposited as a coating onto a Lexan polycarbonate plaque. The coated plague was then dried and cured in an air atmosphere at 130° C. for 18 hours.

Example 9

Epoxy Silane and Xylylenediamine Coating 5.0 g of the resin produced in Example 7 was diluted in 15.0 g of IMS and stirred to give an homogeneous liquid. To this liquid was added 1.02 g of xylylenediamine. The mixture was vigorously stirred for 5 minutes and then deposited as a coating onto a Lexan polycarbonate plaque. The coated plaque was then dried and cured in an air atmosphere at 130° C. for 18 hours.

Example 10

Mixed Epoxy-phenyl Silane Resin

Component A and Component B were separately made up.

Component A. 7.0 g of 3-glycidoxypropyltrimethoxysilane was placed in a beaker, and an intimate mixture of 5.5 g of IMS and 0.80 g of water was added thereto.

Component B. 40.0 g of phenyltrimethoxysilane was placed in a beaker, and an intimate mixture of 37.1 g of IMS and 5.45 g of water was added thereto.

Components A and B were the stirred, separately, in sealed beakers for about one hour, after which they were combined and stirred for about 4 hours, again in a sealed beaker. This mixture was stirred vigorously for 4 hours, and was then poured (or quenched) into 192 g of distilled water. The quenched mixture was stirred vigorously for at least 18 hours before being poured into a large polypropylene container and heated at approximately 50° C. for approximately 6 hours to remove the water. The remaining viscous liquid (resin) was then recovered.

Example 11

Mixed Epoxy-phenyl Silane Diaminooctane Coating 5.0 g of the resin produced in Example 10 was diluted in 15.0 g of IMS and stirred to give an homogeneous liquid. To this liquid was added 0.17 g of diaminooctane. The mixture was vigorously stirred for 5 minutes and then deposited as a coating onto a Lexan polycarbonate plaque. The coated plaque was then dried and cured in an air atmosphere at 130° C. for 18 hours.

Example 12

Cyclohexylepoxysilane Resin

A mixture of 44.9 g of industrial methylated spirit (IMS) and 6.59 g of distilled water were thoroughly stirred and then added to 60.0 g of 2-(3,4-epoxycyclohexyl)ethyltrimethoxysilane. This mixture was stirred vigorously for 4 hours, and was then poured (or quenched) into 223 g of distilled water. The quenched mixture was stirred vigorously for at least 18 hours before being poured into a large polypropylene container and heated at approximately 50° C. for approximately 6 hours to remove the water. The remaining viscous liquid (resin) was then recovered.

Example 13

Cyclohexylepoxysilane Diaminooctane Coating 5.0 g of the resin produced in Example 12 was diluted in 15.0 g of IMS and stirred to give an homogeneous liquid. To this liquid was added 0.20 g of diaminooctane. The mixture was vigorously stirred for 5 minutes and then deposited as a coating onto a Lexan polycarbonate plaque. The coated plaque was then dried and cured in an air atmosphere at 130° C. for 18 hours.

Example 14

Aminosilane Resin

A mixture of 49.9 g of industrial methylated spirit (IMS) and 7.32 g of distilled water were thoroughly stirred and then added to 60.0 g of 3-aminopropyltriethoxysilane. This mixture was stirred vigorously for 4 hours, and was then poured (or quenched) into 234 g of distilled water. The quenched mixture was stirred vigorously for at least 18 hours before being poured into a large polypropylene container and heated at approximately 50° C. for approximately 6 hours to remove the water. The remaining viscous liquid (resin) was then recovered.

Example 15

Mixed Epoxy Resin

Component A and Component B were separately made up.

Component A. 40.0 g of 3-glycidoxypropyltrimethoxysilane was placed in a beaker, and an intimate mixture of 31.1 g of IMS and 4.57 g of water was added thereto.

Component B. 5.0 g of tetraethoxysilane was placed in a beaker, and an intimate mixture of 4.4 g of IMS and 0.65 g of water was added thereto.

Components A and B were the stirred, separately, in sealed beakers for about one hour, after which they were combined and stirred for about 4 hours, again in a sealed beaker. This mixture was stirred vigorously for 4 hours, and was then poured (or quenched) into 172 g of distilled water. The quenched mixture was stirred vigorously for at least 18 hours before being poured into a large polypropylene container and heated at approximately 50° C. for approximately 6 hours to remove the water. The remaining viscous liquid (resin) was then recovered.

Example 16

Dehydration of Resin 1.5 g of the resin produced in Example 4 was dissolved in a mixture of 0.25 g triethylamine and 4.59 of THF. The solution was then placed over dried 4A type molecular sieve. After 24 hours, the solvent was evaporated off and the dehydrated resin was dissolved in 4.5 g IMS and 0.1 g of photoinitiator Irgacure 184 was added. After thorough mixing, the solution was then deposited by flow coating onto a Lexan polycarbonate plague. The coated plaque was air dried for five minutes and then cured using UV light.

Example 17

Capping of Residual Silanols 1.5 g of the resin produced in Example 4 was dissolved in a mixture of 0.25 g triethylamine, 4.5 g of THF and 0.25 g of chlorotrimethylsilane. After 24 hours, the mixture was filtered through a 1 μm filter to remove the solid chloride salt. The solvent was evaporated off and the resin was dissolved in 4.5 g IMS and 0.1 g of photoinitiator Irgacure 184 was added. After thorough mixing the solution was then deposited by flow coating onto a Lexan polycarbonate plaque. The coated plaque was air dried for five minutes and then cured using UV light.

Example 18

Capping of Residual Silanols with $R_2SiY_2$ Type Silane 1.5 g of the resin produced in Example 4 was dissolved in a mixture of 0.25 g triethylamine, 4.5 g of THF and 0.5 g of diethoxydimethylsilane. The solution was then placed over dried 4A type molecular sieve. After 24 hours, the solvent was evaporated off and the resin was dissolved in 4.5 g IMS and 0.1 g or photoinitiator Irgacure 184 was added. After thorough mixing the solution was then deposited by flow coating onto a Lexan polycarbonate plaque. The coated plaque was air dried for five minutes and then cured using UV light.

Example 19

Capping of Residual Silanols with Long Chain Silanes 1.5 g of the resin produced in Example 4 was dissolved in a mixture of 0.25 g triethylamine, 4.5 g of THF and 2 g of hydroxy-terminated polydimethylsiloxane (viscosity=90-150 centi-stokes). The solution was then placed over dried 4A type molecular sieve. After 24 hours, the solvent was evaporated off and the resin was dissolved in 4.5 g IMS and 0.1 g of photoinitiator Irgacure 184 was added. After thorough mixing the solution was then deposited by flow coating onto a Lexan polycarbonate plaque. The coated plaque was air dried for five minutes and then cured using UV light.

Example 20

Incorporation of $R_2SY_2$ Silane into Sol

A mixture of 117.8 g of industrial methylated spirit (IMS), 17.3 grams of water and 0.17 g of 37% HCl were thoroughly stirred and then added to 150.0 g of 3-trimethoxysilylpropyl acrylate. This mixture was stirred for 240 minutes. Separately a mixture of 58.3 g of industrial methylated spirit (IMS), 5.46 grams of water and 0.1 g of 37% HCl were thoroughly stirred and then added to 45.0 g of diethoxydimethylsilane and mixed for five minutes. The two silane solutions were then mixed and stirred together for two hours, and was then poured (or quenched) into 570 g of distilled water. The quenched mixture was stirred vigorously for at least 18 hours before being poured into a large polypropylene container and heated at approximately 50° C. for six hours to remove the water. The remaining liquid resin was then recovered.

Example 21

Dehydration of Resin—Use as Adhesive/Sealant 1.5 g of the resin produced in Example 4 was dissolved in a mixture of 0.25 g triethylamine and 4.5 g of THF. The solution was then placed over dried 4A type molecular sieve. After 24 hours, the solvent was evaporated off and the dehydrated resin was dissolved in 0.5 g IMS and 0.1 g of photoinitiator Irgacure 184 was added together with 0.5 g of urethane acrylate 260Gp25. After thorough mixing the solution was then syringed onto a polyester sheet. A second sheet was placed over the first and the two were pressed together to give a bond line of −50 μm. The sandwich structure was then cured under a UV light for five minutes and the resin mixture gave an adhesive seal.

The invention claimed is:

1. A process for forming a composition comprising organosilsesquioxanes, the process comprising the following steps:
    (1) partially hydrolysing hydrolysable inorganic monomer precursors comprising at least 50 mole % of first hydrolysable inorganic monomer precursors having the formula $RSiY_3$, in which R is an organic group which is stable to hydrolyis and which is the same or different to each other R group, the R—Si bond is a non-hydrolysable bond, and each Y group is the same as or different to each other Y group and is selected from chemically-reactive groups such that each Si—Y bond is hydrolysable to form a Si—OH bond, to form inorganic monomers and allowing partial condensation of the inorganic monomers to form a liquid composition comprising inorganic oligomers, wherein a mineral acid catalyst is used to initiate hydrolysis of the hydrolysable inorganic monomer precursors, wherein an amount of water is added to the hydrolysable monomer precursors so as to achieve hydrolysis of one or at most two of the hydrolysable bonds present in the first hydrolysable monomer precursors;
    (2) prior to complete condensation of the inorganic monomers, quenching the liquid composition with an amount of water which, in combination with the water used in step (1) and any water liberated by condensation of the inorganic monomers in step (1), is in excess of the stoichiometric amount of water required to achieve complete hydrolysis of all the hydrolysable inorganic monomer precursors present, so as to fully hydrolyse the hydrolysable monomer precursors present and favor further condensation; and
    (3) drying the composition to remove essentially all free water and any volatiles and form a dried, essentially water- and volatiles-free composition that is a liquid,
    wherein, when step (1) comprises partially hydrolysing different hydrolysable inorganic monomer precursors, said different hydrolysable inorganic monomer precursors are hydrolyzed separately from one another, followed by partial condensation of the resulting different inorganic monomers, and then mixing the resulting liquid compositions prior to carrying out step (2);

wherein the amount of water used in step (2), in combination with the amount of water used in the hydrolysis of step (1) and any water liberated by condensation in step (1), is at least two times the stoichiometric amount of water required for complete hydrolysis of all the hydrolysable monomer precursors present; and wherein in step (2) of the process, further condensation is allowed to proceed, and the final product is essentially completely condensed.

2. A process according to claim 1, wherein the hydrolysable inorganic monomer precursors comprise more than 60 mole % of first hydrolysable inorganic monomer precursors.

3. A process according to claim 1, wherein the R group in the first hydrolysable inorganic monomer precursors is selected from hydrogen and (cyclo)alkyl, aryl, alkenyl, and mixtures thereof, optionally substituted with groups selected from epoxy, vinyl, and (meth)acrylic groups.

4. A process according to claim 1, wherein the Y groups in the first hydrolysable monomer precursors are selected from alkoxy, acetoxy and nitrate groups and halogen atoms.

5. A process according to claim 1, wherein when step (1) comprises partially hydrolysing different hydrolysable inorganic monomer precursors said different hydrolysable inorganic monomer precursors are hydrolysed separately from one another, followed by partial condensation of the resulting different inorganic monomers, and then mixing of the resulting liquid compositions prior to carrying out step (2).

6. A process according to claim 1, wherein the first hydrolysable monomer precursors comprise molecules having different R groups, wherein in step (1) the different first hydrolysable monomer precursors are hydrolysed separately from one another, and allowed to partially condense, and the resulting liquid compositions are then mixed together prior to carrying out step (2).

7. A process according to claim 1, wherein the hydrolysable inorganic monomer precursors additionally comprise second hydrolysable monomer precursors having the formula $R_nSiY_{4-n}$ in which n is 0, 2 or 3, each R—Si bond is a non-hydrolysable bond, R is an organic group and each R group is the same as or different to each other R group, and each Y group is the same as or different to each other Y group and is selected from chemically-reactive groups such that each Si—Y bond is hydrolysable to Si—OH, and wherein in step (1) the first and second hydrolysable monomer precursors are partially hydrolysed separately from one another, and allowed to partially condense, and the resulting liquid compositions are then mixed together prior to carrying out step (2).

8. A process according to claim 7, wherein the second hydrolysable inorganic monomer precursors have the formula $SiY_4$.

9. A process according to claim 1, wherein the hydrolysable inorganic monomer precursors additionally comprise hydrolysable monomer precursors having the formula $MY_n$, in which M is a metal, n is the valency of the metal, and each Y group is the same as or different to each other Y group and is selected from chemically-reactive groups such that each M—Y bond is hydrolysable to a M-OH bond, and wherein in step (1) the different hydrolysable monomer precursors are partially hydrolysed separately from one another, and allowed to partially condense, and the resulting liquid compositions are then mixed together prior to carrying out step (2).

10. A process according to claim 1, wherein the hydrolysable inorganic monomer precursors additionally comprise hydrolysable monomer precursors having the formula $(R_2Si)_xY_2$, in which x=1, each R—Si bond is a nonhydrolysable bond, R is an organic group and each R group is the same as or different to each other R group, and each Y group is the same as or different to each other Y group and is selected from chemically-reactive groups such that each Si—Y bond is hydrolysable to Si—OH, and wherein in step (1) the different hydrolysable monomer precursors are partially hydrolysed separately from one another, and allowed to partially condense, and the resulting liquid compositions are then mixed together prior to carrying out step (2).

11. A process according to claim 1, wherein in step (1) at least 80 mole % of the first hydrolysable monomer precursors undergo hydrolysis and condensation via one of the Si—Y bonds to form inorganic oligomers having the formula $RY_2$—Si—O—$SiY_2R$.

12. A process according to claim 1, which comprises, as step (4), dehydrating the composition obtained in step (3) to obtain a dehydrated composition.

13. A process according to claim 1, which further comprises cross-linking the composition obtained in step (3) via residual silanols present in the composition to obtain a cross-linked composition.

14. A process according to claim 1, which further comprises mixing the composition obtained in step (3) with organic monomers or oligomers.

15. A process according to claim 12, which further comprises mixing the dehydrated composition obtained in step (4) with organic monomers or oligomers.

16. A process according to claim 13, which further comprises mixing the cross-linked composition obtained with organic monomers or oligomers.

17. A process according to claim 14, which further comprises polymerizing the organic monomers or oligomers.

18. A process according to claim 1, which comprises mixing the composition obtained in step (3) with a liquid organic polymer.

19. A process according to claim 12, which further comprises mixing the dehydrated composition obtained in step (4) with a liquid organic polymer.

20. A process according to claim 13, which further comprises mixing the cross-linked composition obtained with a liquid organic polymer.

21. A process according to claim 1, which further comprises cross-linking the composition obtained in step (3) via the R groups to obtain a cross-linked composition.

22. A process according to claim 12, which further comprises cross-linking the composition obtained in step (3) via the R groups to obtain a cross-linked composition.

23. A process for providing a coating on a substrate comprising, carrying out the process of claim 1 to produce a composition comprising organosilsesquioxanes, applying to the substrate the composition, and optionally cross-linking the composition.

24. A process for providing a coating on a substrate comprising, carrying out the process of claim 1 to produce a composition comprising organosilsesquioxanes, applying to the substrate the composition, polymerising the organic monomers or oligomers and optionally cross-linking the composition.

25. A process according to claim 23, wherein the substrate is selected from thermoplastic polymeric substrates.

26. A process according to claim 23, wherein the substrate is selected from metals, including soft metals such as aluminium, brass and silver.

27. A process for forming an article comprising, carrying out the process of claim 1 to produce a composition comprising organosilsesquioxanes and shaping the composition.

28. A process for bonding together at least two articles comprising, carrying out the process of claim 1 to produce a composition comprising organosilsesquioxanes, applying to the surface of one or each article the composition, bringing the surfaces into contact with one another, and then cross-linking the composition to form a bond.

29. A process according to claim 24, wherein the substrate is selected from thermoplastic polymeric substrates.

30. A process according to claim 24, wherein the substrate is selected from metals, including soft metals such as aluminium, brass and silver.

31. A process according to claim 1, wherein the hydrolysable inorganic monomer precursors comprise at least 70 mole % of first hydrolysable inorganic monomer precursors.

32. A process according to claim 1, wherein the hydrolysable inorganic monomer precursors comprise at least 80 mole % of first hydrolysable inorganic monomer precursors.

33. A process according to claim 1, wherein in step (1) at least 90 mole % of the first hydrolysable monomer precursors undergo hydrolysis and condensation via one of the Si—Y bonds to form inorganic oligomers having the formula $RY_2$—Si—O—$SiY_2$R.

34. A process according to claim 29, wherein the substrate is selected from polycarbonate and acrylic resins.

35. A process according to claim 4, wherein the Y groups in the first hydrolysable monomer precursors are alkoxy groups.

36. A process for forming a composition comprising organosilsesquioxanes, the process comprising the following steps:
(1) partially hydrolysing hydrolysable inorganic monomer precursors comprising at least 50 mole % of first hydrolysable inorganic monomer precursors having the formula $RSiY_3$, in which R is an organic group which is stable to hydrolyis and which is the same or different to each other R group, the R—Si bond is a non-hydrolysable bond, and each Y group is the same as or different to each other Y group and is selected from chemically-reactive groups such that each Si—Y bond is hydrolysable to form a Si—OH bond, to form inorganic monomers and allowing partial condensation of the inorganic monomers to form a liquid composition comprising inorganic oligomers, wherein a mineral acid catalyst is used to initiate hydrolysis of the hydrolysable inorganic monomer precursors, wherein an amount of water is added to the hydrolysable monomer precursors so as to achieve hydrolysis of one or at most two of the hydrolysable bonds present in the first hydrolysable monomer precursors;
(2) prior to complete condensation of the inorganic monomers, quenching the liquid composition with an amount of water which, in combination with the water used in step (1) and any water liberated by condensation of the inorganic monomers in step (1), is in excess of the stoichiometric amount of water required to achieve complete hydrolysis of all the hydrolysable inorganic monomer precursors present, so as to fully hydrolyse the hydrolysable monomer precursors present and favor further condensation; and
(3) drying the composition to remove essentially all free water and any volatiles and form a dried, essentially water- and volatiles-free composition that is a liquid,
wherein, when step (1) comprises partially hydrolysing different hydrolysable inorganic monomer precursors, said different hydrolysable inorganic monomer precursors are hydrolyzed separately from one another, followed by partial condensation of the resulting different inorganic monomers, and then mixing the resulting liquid compositions prior to carrying out step (2);
wherein the amount of water used in step (2), in combination with the amount of water used in the hydrolysis of step (1) and any water liberated by condensation in step (1), is at least five times the stoichiometric amount of water required for complete hydrolysis of all the hydrolysable monomer precursors present; and
wherein in step (2) of the process, further condensation is allowed to proceed, and the final product is essentially completely condensed.

37. A process for forming a composition comprising organosilsesquioxanes, the process comprising the following steps:
(1) separately and partially hydrolyzing, using a mineral acid catalyst, different hydrolysable inorganic monomer precursors, at least 50 mole % of which comprise first hydrolysable inorganic monomer precursors having the formula $RSiY_3$, in which R is an organic group which is stable to hydrolyis and which is the same or different to each other R group, the R—Si bond is a non-hydrolysable bond, and each Y group is the same as or different to each other Y group and is selected from chemically-reactive groups such that each Si—Y bond is hydrolysable to form a Si—OH bond, to form inorganic monomers, wherein the first hydrolysable inorganic monomer precursor is hydrolyzed in the presence of an amount of water to achieve hydrolysis of at least one and at most two of the hydrolysable bonds present in the first hydrolysable monomer precursors;
(2) separately allowing partial condensation of the inorganic monomers to form a plurality of intermediate liquid compositions comprising inorganic oligomers;
(3) mixing together the plurality of intermediate liquid compositions to form a mixed intermediate liquid composition;
(4) prior to complete condensation of the inorganic monomers, quenching the mixed intermediate liquid composition with an amount of water which, in combination with the water used in step (1) and any water liberated by partial condensation of the inorganic monomers in step (2), is at least two times the stoichiometric amount of water required to achieve complete hydrolysis of all the hydrolysable inorganic monomer precursors present, so as to formed a quenched intermediate liquid composition and fully hydrolyse the hydrolysable monomer precursors present and favor further condensation;
(5) allowing further condensation of the quenched intermediate liquid composition; and
(6) drying the composition to remove essentially all free water and any volatiles and form a dried, essentially water- and volatiles-free composition that is a liquid and that is essentially completely condensed.

* * * * *